United States Patent [19]
Brock

[11] Patent Number: 5,797,405
[45] Date of Patent: Aug. 25, 1998

[54] THUMB SUCKING DETERRENT DEVICE AND METHOD

[76] Inventor: Lunetta R. Brock, 108 N. Bayview Dr., Fairhope, Ala. 36532

[21] Appl. No.: 855,403

[22] Filed: May 13, 1997

[51] Int. Cl.$^6$ .................................................. A61C 5/37
[52] U.S. Cl. ........................... 128/878; 128/879; 128/880
[58] Field of Search ........................... 128/878, 879, 128/880, 898; 2/16–21, 161 R, 161 A, 163, 159, 167

[56] References Cited

U.S. PATENT DOCUMENTS

| | | | |
|---|---|---|---|
| 2,225,896 | 12/1940 | Belknap | 128/880 |
| 2,498,122 | 2/1950 | Haniuk | 128/880 |
| 2,633,126 | 3/1953 | Newmark | 128/133 |
| 2,742,898 | 4/1956 | Beaudry | 128/880 |
| 4,396,014 | 8/1983 | Pace et al. | 128/133 |
| 4,665,907 | 5/1987 | Leverette | 128/133 |
| 4,692,748 | 9/1987 | Pinsak et al. | 340/133 |
| 4,787,376 | 11/1988 | Eisenberg | 128/880 |
| 5,010,901 | 4/1991 | Pales | 128/880 |
| 5,474,093 | 12/1995 | Pettiet | 128/880 |
| 5,515,870 | 5/1996 | Zilber | 128/878 |

Primary Examiner—Michael A. Brown
Attorney, Agent, or Firm—Joseph N. Breaux

[57] ABSTRACT

A thumb sucking deterrent device that includes a cloth palm cover structure having a palm chamber formed therein for receiving the palm of a hand, the palm cover structure including an insertion opening and a finger extension opening in connection with the palm chamber; a thumb shield structure having a thumb receiving chamber formed therein and in connection with the palm chamber of the palm cover structure that is constructed of a terry cloth fabric having at least one surface covered with a plurality of outwardly extending terry cloth loops, the plurality of terry cloth loops extending outwardly, the thumb shield structure having a tip portion at a terminal end thereof; and an anti-sucking latex rubber coating covering the tip portion of the thumb shield structure, the anti-sucking latex rubber coating be applied in a manner such that the latex rubber coating covers a second plurality of terry cloth loops covering the tip portion to form a third plurality of sucking deterrent protrusions, each sucking deterrent protrusion including at least one terry cloth loop of the third plurality of terry cloth loops that is covered with a latex rubber coating. The thumb sucking deterrent method includes the step of providing three pairs of the thumb sucking deterrent device of the present invention and the step of maintaining one of the three pairs of thumb sucking deterrent devices on the hands of the child at all times.

17 Claims, 2 Drawing Sheets

THUMB SUCKING DETERRENT DEVICE AND METHOD

TECHNICAL FIELD

The present invention relates to devices and methods for deterring thumb sucking behavior in young children and more particularly to a thumb sucking deterrent device and method wherein the thumb sucking deterrent device includes a palm cover structure having a palm chamber formed therein for receiving the palm area of a hand, the palm cover structure being constructed from a cloth material and including an insertion opening and a finger extension opening in connection with the palm chamber; a thumb shield structure having a thumb receiving chamber formed therein and in connection with the palm chamber of the palm cover structure that is constructed of a terry cloth fabric having at least one surface covered with a plurality of outwardly extending terry cloth loops, the plurality of terry cloth loops extending outwardly, the thumb shield structure having a tip portion at a terminal end thereof; and an anti-sucking latex rubber coating covering the tip portion of the thumb shield structure, portion to form sucking deterrent protrusions, each sucking deterrent protrusion including at least one terry cloth loop and wherein the thumb sucking deterrent method includes the step of providing three pairs of the thumb sucking deterrent device of the present invention and the step of maintaining one of the three pairs of thumb sucking deterrent devices on the hands of the child at all times.

BACKGROUND OF THE INVENTION

Because thumb sucking can lead to teeth and mouth deformities and can also cause a child much embarrassment, it is desirable to deter development and practice of this behavior. Although it is desirable to deter development and practice of thumb sucking, it is often difficult in practice to do so. It would be a benefit, therefore, to those parents and care givers seeking to deter either the development or practice of thumb sucking behavior to have a device to assist them. Because the child often derives some satisfaction from this sucking behavior, it would be a benefit if the thumb sucking deterrent device eliminated this satisfaction and replaced it with an undesirable sensation when sucking behavior is practiced. In addition, because many young mothers are inexperienced in teaching young children to stop thumb sucking behavior, it would be a benefit to have an easily practiced method for these mothers to follow to deter thumb sucking behavior.

SUMMARY OF THE INVENTION

It is thus an object of the invention to provide a thumb sucking deterrent device.

It is a further object of the invention to provide a thumb sucking deterrent device that includes a mechanism for creating undesirable sensations in the mouth of the child when thumb sucking behavior is practiced.

It is a still further object of the invention to provide a thumb sucking deterrent device that includes a palm cover structure having a palm chamber formed therein for receiving the palm area of a hand, the palm cover structure being constructed from a cloth material and including an insertion opening and a finger extension opening in connection with the palm chamber; a thumb shield structure having a thumb receiving chamber formed therein and in connection with the palm chamber of the palm cover structure that is constructed of a terry cloth fabric having at least one surface covered with a plurality of outwardly extending terry cloth loops, the plurality of terry cloth loops extending outwardly, the thumb shield structure having a tip portion at a terminal end thereof; and an anti-sucking latex rubber coating covering the tip portion of the thumb shield structure, the anti-sucking latex rubber coating covering the tip portion to form sucking deterrent protrusions, each sucking deterrent protrusion including at least one terry cloth loop.

It is a still further object of the invention to provide a thumb sucking deterrent device that accomplishes some or all of the above objects in combination.

It is a still further object of the invention to provide a thumb sucking deterrent method.

It is a still further object of the invention to provide a thumb sucking deterrent method that is easily practiced.

It is a still further object of the invention to provide a thumb sucking deterrent method that includes the step of providing three pairs of the thumb sucking deterrent device wherein each thumb sucking deterrent device includes a palm cover structure having a palm chamber formed therein for receiving the palm area of a hand, the palm cover structure being constructed from a cloth material and including an insertion opening and a finger extension opening in connection with the palm chamber; a thumb shield structure having a thumb receiving chamber formed therein and in connection with the palm chamber of the palm cover structure that is constructed of a terry cloth fabric having at least one surface covered with a plurality of outwardly extending terry cloth loops, the plurality of terry cloth loops extending outwardly, the thumb shield structure having a tip portion at a terminal end thereof; and an anti-sucking latex rubber coating covering the tip portion of the thumb shield structure, the anti-sucking latex rubber coating covering the tip portion to form sucking deterrent protrusions, each sucking deterrent protrusion including at least one terry cloth loop; and the step of maintaining one of the three pairs of thumb sucking deterrent devices on the hands of the child at all times.

Accordingly, a thumb sucking deterrent device is provided. The thumb sucking deterrent device includes a palm cover structure having a palm chamber formed therein for receiving the palm area of a hand, the palm cover structure being constructed from a cloth material and including an insertion opening and a finger extension opening in connection with the palm chamber; a thumb shield structure having a thumb receiving chamber formed therein and in connection with the palm chamber of the palm cover structure that is constructed of a terry cloth fabric having at least one surface covered with a plurality of outwardly extending terry cloth loops, the plurality of terry cloth loops extending outwardly, the thumb shield structure having a tip portion at a terminal end thereof; and an anti-sucking latex rubber coating covering the tip portion of the thumb shield structure, the anti-sucking latex rubber coating covering the tip portion to form sucking deterrent protrusions, each sucking deterrent protrusion including at least one terry cloth loop. In a preferred embodiment the palm cover structure is constructed from terry cloth fabric. In another preferred embodiment the palm cover structure and the thumb shield structure are constructed from a single cut-out section of terry cloth fabric.

BRIEF DESCRIPTION OF DRAWINGS

For a further understanding of the nature and objects of the present invention, reference should be made to the following detailed description, taken in conjunction with the

Figure 1:
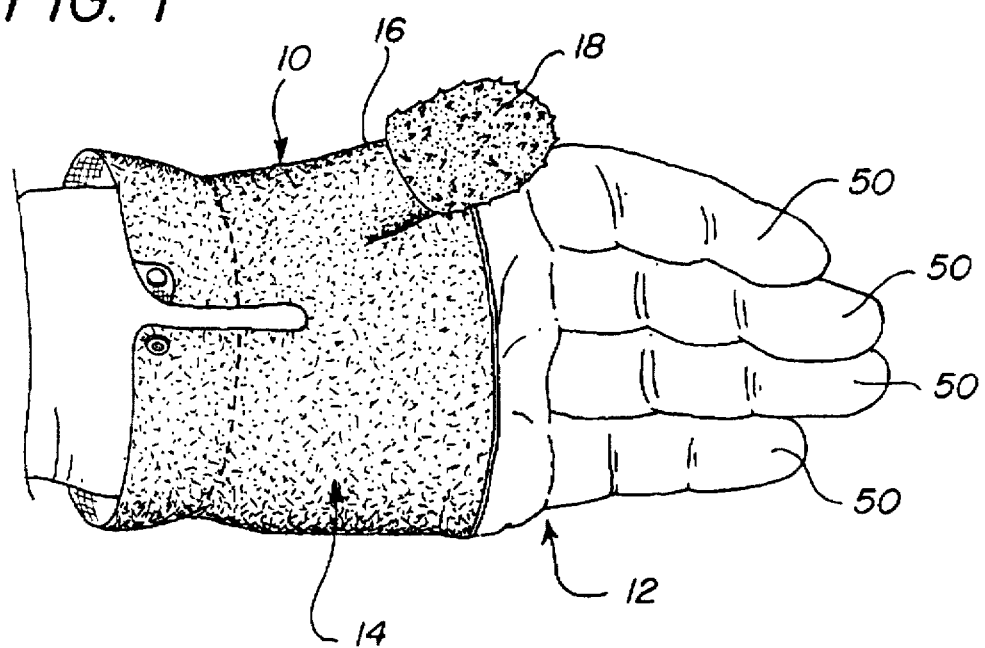

3 accompanying drawings, in which like elements are given the same or analogous reference numbers and wherein:

FIG. 1 is a perspective view of an exemplary embodiment of the thumb sucking deterrent device of the present invention positioned onto the hand of a child with the palm of the hand positioned within the palm cover structure of the deterrent device, the thumb of the hand positioned within the thumb shield structure of the deterrent device, and the fingers of the hand extending out through the finger opening of the deterrent device.

Figure 2:
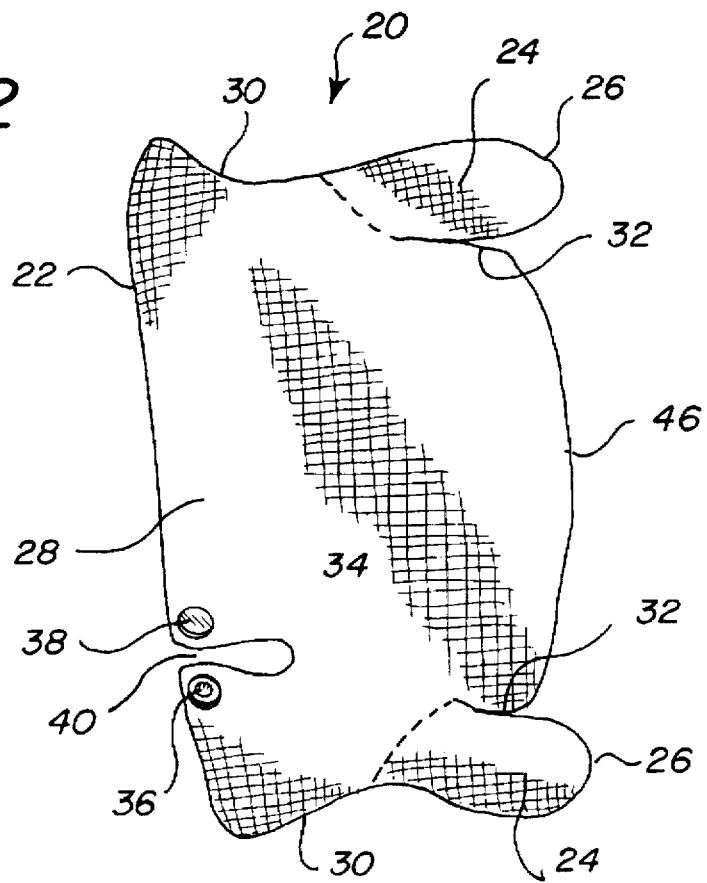

FIG. 2 is a plan view of an exemplary terry cloth fabric cut-out that is stitched along opposed edges to form the fabric palm cover and thumb shield structures.

Figure 3:
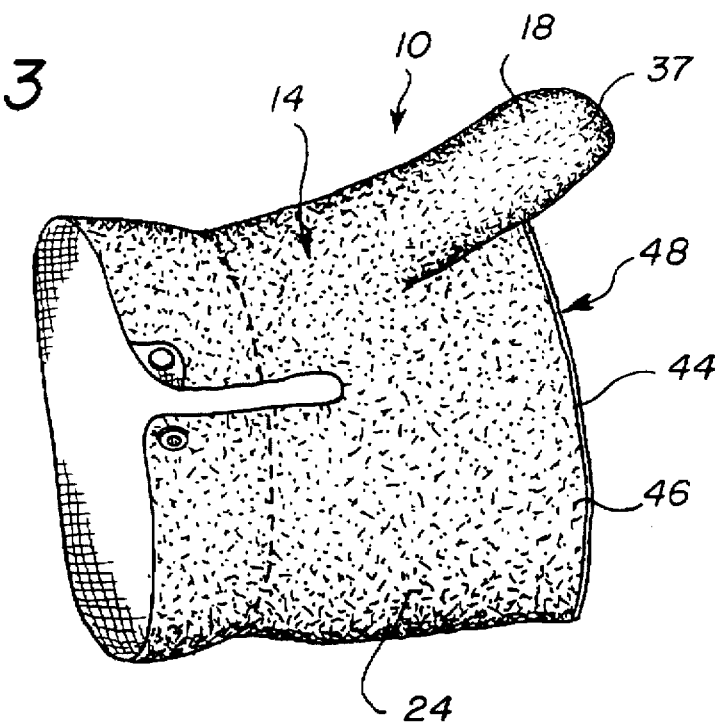

FIG. 3 is a perspective view showing the palm cover and thumb shield structure constructed by stitching the fabric cut-out of FIG. 2 along the opposed edges.

Figure 4:
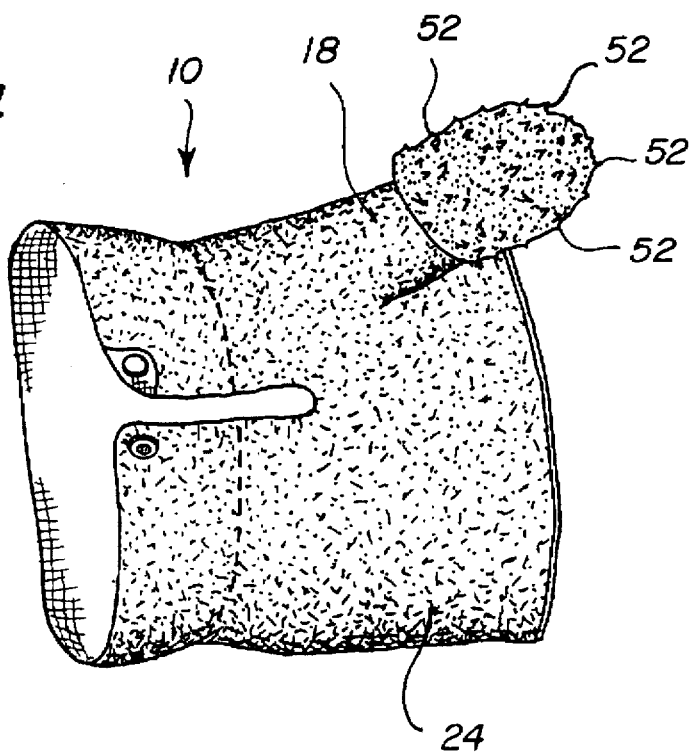

FIG. 4 is a perspective view showing the palm cover and thumb shield structure of FIG. 3 after the thumb shield structure has been coated with anti-sucking latex rubber coating to form the sucking deterrent protrusions.

DESCRIPTION OF THE EXEMPLARY EMBODIMENT

FIG. 1 shows an exemplary embodiment of the thumb sucking deterrent device of the present invention, generally designated 10, positioned onto the hand, generally designated 12, of a child. Deterrent device 10 includes a palm cover structure, generally designated 14; a thumb shield structure, generally designated 16; and an anti-sucking latex rubber coating, generally designated 18.

With reference to FIG. 2, in this embodiment palm cover structure 14 (FIG. 1) and thumb shield structure 18 (FIG. 1) are formed from a single cut-out section, generally designated 20, of high pile loop density terry cloth fabric having a fabric side 22 and a pile side 24 (designated in FIGS. 3 and 4). Cut-out section 20 includes two thumb sections 24 that when stitches together along the perimeter edges 26 form a thumb shield structure 18 having a tip portion 37 (FIG. 3) for receiving the thumb of a child. A central portion 28 is stitched together along perimeter edges 30 and 32 to form a tubular palm cover structure 14 (FIG. 3) open at either end. A wrist securing slit 34 is formed into central portion 28 and male and female snap fastener halves 36, 38 installed one either side of a slit opening 40.

With reference to FIG. 3, a length of elastic material 44 is stitched to the forward edge 46 (also shown in FIG. 2) of palm cover structure 14 to provide an elasticized finger opening 48 through which fingers 50 (FIG. 1) extend when deterrent device 10 is positioned onto the hand during use. When all stitching is accomplished, thumb shield structure 18 and palm cover portion 14 together resemble a glove with the four fingers removed.

With reference now to FIG. 4, manufacture of deterrent device 10 is completed by coating tip portion 37 (FIG. 3) of thumb shield structure 18 with latex rubber in a manner such that individual and groups of pile loops are coated with latex rubber and form a number of discrete sucking deterrent protrusions 52.

In a second aspect of the invention an exemplary method of deterring thumb sucking includes the step of providing three pairs of thumb sucking devices 10 and the step of maintaining one pair of thumb sucking deterrent devices 10 on the hands of the child at all times for a period of time, preferably between one and four weeks. After the time period has passed, thumb sucking devices 10 can be removed and the child carefully observed for thumb sucking activity. If thumb sucking activity is observed, wear of a pair of thumb sucking devices 10 is reinstated for an additional period of time.

It can be seen from the preceding description that a thumb sucking deterrent device has been provided that includes a mechanism for creating undesirable sensations in the mouth of the child when thumb sucking behavior is practiced; that includes a palm cover structure having a palm chamber formed therein for receiving the palm area of a hand, the palm cover structure being constructed from a cloth material and including an insertion opening and a finger extension opening in connection with the palm chamber; a thumb shield structure having a thumb receiving chamber formed therein and in connection with the palm chamber of the palm cover structure that is constructed of a terry cloth fabric having at least one surface covered with a plurality of outwardly extending terry cloth loops, the plurality of terry cloth loops extending outwardly, the thumb shield structure having a tip portion at a terminal end thereof; and an anti-sucking latex rubber coating covering the tip portion of the thumb shield structure sucking deterrent protrusions, each sucking deterrent protrusion including at least one terry cloth loop. It can also been seen from the preceding description that a method of deterring thumb sucking has been provided that is easily practiced; and that includes the step of providing three pairs of the thumb sucking deterrent device wherein each thumb sucking deterrent device includes a palm cover structure having a palm chamber formed therein for receiving the palm area of a hand, the palm cover structure being constructed from a cloth material and including an insertion opening and a finger extension opening in connection with the palm chamber; a thumb shield structure having a thumb receiving chamber formed therein and in connection with the palm chamber of the palm cover structure that is constructed of a terry cloth fabric having at least one surface covered with a plurality of outwardly extending terry cloth loops, the plurality of terry cloth loops extending outwardly, the thumb shield structure having a tip portion at a terminal end thereof; and an anti-sucking latex rubber coating covering the tip portion of the thumb shield structure to form sucking deterrent protrusions, each sucking deterrent protrusion including at least one terry cloth loop of the third plurality of terry cloth loops that is covered with a latex rubber coating; and the step of maintaining one of the three pairs of thumb sucking deterrent devices on the hands of the child at all times.

It is noted that the embodiment of the thumb sucking deterrent device described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A thumb sucking deterrent device comprising:

a palm cover structure having a palm chamber formed therein for receiving said palm area of a hand, said palm cover structure being constructed from a cloth material and including an insertion opening and a finger extension opening in connection with said palm chamber;

a thumb shield structure having a thumb receiving chamber formed therein and in connection with said palm chamber of said palm cover structure that is constructed of a terry cloth fabric having at least one surface covered with a plurality of outwardly extending terry cloth loops, said plurality of terry cloth loops extending outwardly, said thumb shield structure having a tip portion at a terminal end thereof; and an anti-sucking latex rubber coating covering said tip portion of said thumb shield structure, said anti-sucking latex rubber coating some of said terry cloth loops covering said tip portion to form sucking deterrent protrusions, each said sucking deterrent protrusion including at least one terry cloth loop.

2. The thumb sucking deterrent device of claim 1, wherein:

said palm cover structure is constructed from terry cloth fabric.

3. The thumb sucking deterrent device of claim 2, wherein:

said palm cover structure and said thumb shield structure are constructed from a single cut-out section of terry cloth fabric.

4. The thumb sucking deterrent device of claim 3 wherein:

an edge portion of said palm cover structure that defines said finger extension opening has a length of elastic material secured thereto in a manner to constrict said finger extension opening.

5. The thumb sucking deterrent device of claim 4 wherein:

said palm cover structure has a wrist securing slit formed therein and further includes a fastener for securing together either side of said palm cover structure defining a slit opening in connection with said wrist securing slit.

6. The thumb sucking deterrent device of claim 3 wherein:

said palm cover structure has a wrist securing slit formed therein and further includes a fastener for securing together either side of said palm cover structure defining a slit opening in connection with said wrist securing slit.

7. The thumb sucking deterrent device of claim 2 wherein:

an edge portion of said palm cover structure that defines said finger extension opening has a length of elastic material secured thereto in a manner to constrict said finger extension opening.

8. The thumb sucking deterrent device of claim 7 wherein:

said palm cover structure has a wrist securing slit formed therein and further includes a fastener for securing together either side of said palm cover structure defining a slit opening in connection with said wrist securing slit.

9. The thumb sucking deterrent device of claim 2 wherein:

said palm cover structure has a wrist securing slit formed therein and further includes a fastener for securing together either side of said palm cover structure defining a slit opening in connection with said wrist securing slit.

10. The thumb sucking deterrent device of claim 1, wherein:

said palm cover structure and said thumb shield structure are constructed from a single cut-out section of terry cloth fabric.

11. The thumb sucking deterrent device of claim 10 wherein:

an edge portion of said palm cover structure that defines said finger extension opening has a length of elastic material secured thereto in a manner to constrict said finger extension opening.

12. The thumb sucking deterrent device of claim 11 wherein:

said palm cover structure has a wrist securing slit formed therein and further includes a fastener for securing together either side of said palm cover structure defining a slit opening in connection with said wrist securing slit.

13. The thumb sucking deterrent device of claim 10 wherein:

said palm cover structure has a wrist securing slit formed therein and further includes a fastener for securing together either side of said palm cover structure defining a slit opening in connection with said wrist securing slit.

14. The thumb sucking deterrent device of claim 1 wherein:

an edge portion of said palm cover structure that defines said finger extension opening has a length of elastic material secured thereto in a manner to constrict said finger extension opening.

15. The thumb sucking deterrent device of claim 14 wherein:

said palm cover structure has a wrist securing slit formed therein and further includes a fastener for securing together either side of said palm cover structure defining a slit opening in connection with said wrist securing slit.

16. The thumb sucking deterrent device of claim 1 wherein:

said palm cover structure has a wrist securing slit formed therein and further includes a fastener for securing together either side of said palm cover structure defining a slit opening in connection with said wrist securing slit.

17. A method of deterring thumb sucking behavior of a child comprising the steps of:

a) providing six thumb sucking deterrent devices each comprising:

a palm cover structure having a palm chamber formed therein for receiving said palm area of a hand, said palm cover structure being constructed from a cloth material and including an insertion opening and a finger extension opening in connection with said palm chamber;

a thumb shield structure having a thumb receiving chamber formed therein and in connection with said palm chamber of said palm cover structure that is constructed of a terry cloth fabric having at least one surface covered with a plurality of outwardly extending terry cloth loops, said plurality of terry cloth loops extending outwardly, said thumb shield structure having a tip portion at a terminal end thereof; and an anti-sucking latex rubber coating covering said tip portion said thumb shield structure, said anti-sucking latex rubber coating some of said terry cloth loops covering said tip portion to form sucking deterrent protrusions, each said sucking deterrent protrusion including at least one terry cloth loop; and b) maintaining two of said six thumb sucking deterrent devices on the hands of the child at all times for a period of time between one and four weeks.

* * * * *